United States Patent [19]

Quaglia

[11] 4,262,087
[45] Apr. 14, 1981

[54] PHOTOGRAPHIC ELEMENTS CONTAINING 5-PYRAZOLONE MAGENTA COUPLERS

[75] Inventor: Andrea Quaglia, Albisola M., Italy

[73] Assignee: Minnesota Mining and Manufacturing Company, St. Paul, Minn.

[21] Appl. No.: 9,426

[22] Filed: Feb. 5, 1979

[30] Foreign Application Priority Data

Feb. 17, 1978 [IT] Italy ................................ 48086 A/78

[51] Int. Cl.³ ................................................ G03C 1/40
[52] U.S. Cl. ..................................... 430/503; 430/387; 430/; 430/558
[58] Field of Search ................. 430/387, 555, 558, 503

[56] References Cited

U.S. PATENT DOCUMENTS

| 2,435,182 | 1/1948 | Long et al. | 260/162 |
| 4,076,533 | 2/1978 | Ota et al. | 430/387 |

FOREIGN PATENT DOCUMENTS

2536191  3/1976  Fed. Rep. of Germany ........... 430/555

*Primary Examiner*—J. Travis Brown
*Attorney, Agent, or Firm*—Cruzan Alexander; Donald M. Sell; Mark A. Litman

[57] ABSTRACT

2-equivalent 5-pyrazolone magenta couplers having a 1,2,4-triazole with a halogen in the 3-position and a hydrogen in the 5-position thereof are particularly useful in color photographic emulsions.

12 Claims, No Drawings

PHOTOGRAPHIC ELEMENTS CONTAINING 5-PYRAZOLONE MAGENTA COUPLERS

The present invention relates to couplers for photographic use, to photographic elements including them and to photographic elements including the dyes derived therefrom upon color development.

Particularly, the present invention refers to 2-equivalent 5-pyrazolone magenta couplers.

It is known that couplers are used in color photography which in presence of exposed silver halide are capable of reacting with p-phenylene diamine developers to form a dye image-wise distributed in the developed photographic element. Such couplers must be per se stable in every storage condition as well as the dyes derived therefrom. They normally require four equivalents of reduced silver halide to form a dye mole but photographic couplers requiring only two equivalents of silver halide to be reduced to form a dye mole have been recently described.

Such couplers can be used in a developing bath (bath couplers)—and in this case they must not bear ballasting groups which hinder their diffusion—or can be used in the light-sensitive element associated to the silver halide emulsion contained therein. In this case they bear terminal alyphatic chains which make the coupler molecule a non-diffusing one.

Such non-diffusing couplers can be introduced, in a known way, into the photographic layer containing them (generally the silver halide emulsion layer or a layer adjacent thereto) either in an alkaline water solution (in this case at least an acid solubilizing group of the $SO_3H$ or $COOH$ type must be introduced into the coupler molecule itself), or dissolved in a high-boiling organic solvent dispersed in the coating composition of the layer.

Briefly, this second method, which at present is the preferred one, is called "dispersion method" and substantially consists first of dissolving the coupler in a substantially water-immiscible organic solvent and then of dispersing the so-obtained solution as extremely tiny droplets into a hydrophilic colloidal binder. Gelatin is the preferred hydrophilic colloidal binder, but other known polymeric colloidal binders can also be used. (A description of the dispersion method can be found in U.S. Pat. Nos. 2,322,027; 2,801,170; 2,801,171 and 2,991,177).

The dye formation reaction must have certain characteristics, desired in the color photographic process, which involve for instance fineness of the image grain and modulated contrast (as for instance described in the U.S. Pat. Nos. 2,689,793; 2,742,832; 2,998,314 and 3,227,554).

In addition to what above, the absorption characteristics of the dye formed upon development of the couplers within a photographic element are very important to obtain color images of the desired color balance (which is generally different in the various materials for use in photography, such as for example color print, color positive and color paper materials).

Typical classes of coupler compounds used in photography are 3-aniline-5-pyrazolone compounds and 3-acylamino-5-pyrazolone compounds as described in U.S. Pat. Nos. 2,311,082, 2,983,611, 3,127,269, 3,152,896, 2,600,788, 3,062,653.

A high degree of criticality in the behavior of the 2-equivalent 5-pyrazolone couplers is believed to be responsible of the non use of these couplers although two-equivalent couplers have been described in many previous patents (see for example U.S. Pat. Nos. 3,419,391, and some recent attempts as described in DT-OS 2,424,467, 2,501,260, 2,536,191, 2,651,363 and 2,703,589).

As said in a recent application of the same Applicant (U.S. Ser. No. 885,208 filed on Mar. 10, 1978) it was very difficult to find out two-equivalent magenta couplers of practical value in the photographic industry. According to it some useful 2-equivalent magenta couplers have been found of the 3-aniline-5-pyrazolone type.

Although the above invention is believed to be of great value to the industry, it is highly desirable to find out 2-equivalent 5-pyrazolone couplers of the 3-acylamino type because they give absorption characteristics to the dyes obtained therefrom (upon color development with p-phenylene diamine developers) as preferably desired in color negative and color reversal photographic films.

The present invention refers to a 3-halogen-1,2,4-triazole substituents, having a hydrogen atom in 5-position thereof, attached to the 4-position of the 5-pyrazolone nucleus of a 3-acylamine-5-pyrazolone coupler.

The above couplers of the present invention showed to originate, upon color development, dyes of the nuance desired, at least in some cases, in the photographic industry and to have very good characteristics from the point of view of their stability and capability of reacting with fine grain and modulated contrast without any excessive level of fog.

As far as 3-acylamine-5-pyrazolone couplers of the present invention are concerned, the 4-substitution of the 5-pyrazolone nucleus turned out to be more crytical than expected. Particularly, the substituents attached to the 1,2,4-triazole substituent attached to said 4-position of the 5-pyrazolone nucleus have shown a great influence on the properties of the obtained couplers.

In fact, some of the couplers described in previous patents have been prepared for comparison purposes, for example having a 3-methyl-1,2,4-triazole, a 3-phenyl-1,2,4-triazole, a 3,5-dimethyl-1,2,4-triazole or a 3-Cl-5-methyl-1,2,4-triazole nucleus attached to the 4-position of a 3-acylamino-5-pyrazolone coupler, but no satisfactory results have been obtained (substantially because of found either too low or too high reactivity).

According to the experience of the Applicant, the 5-posItion of the 1,2,4-triazole substituent cannot have any substituent instead of hydrogen in the couplers of the present invention.

Furthermore and particularly, according to some experiments done by the Applicant, the substituents attached to the phenyl group in the 1-position in the 5-pyrazolone nucleus have a particular influence when combined with a 1,2,4-triazole attached to the 4-position of the 5-pyrazolone nucleus. The so-obtained couplers have shown higher fog when said phenyl group was substituted with a chlorine atom in the 2-position and methyl groups in the 4 and 6-positions with respect to the same couplers having chloro-substituents in the 2, 4 and 6-positions of the same 1-phenyl.

In its widest aspect, the present invention refers therefore to 2-equivalent photographic couplers derived from 1-phenyl-3-acylamino-5-pyrazolone characterized by having attached to the 4-position thereof a 1,2,4-triazole substituted in the 3-position with a halogen atom and having in the 5-position a hydrogen atom, the phenyl group in the 1-position having at least 1-halogen atom as a substituent.

The present invention in particular refers to the couplers as per above wherein the substituents of the 1-phenyl group are chosen among halogen (preferably chlorine and bromine, more preferably chlorine), alkyl and alkoxy groups having from 1 to 3 carbon atoms. Preferably, the present invention refers to the couplers as per above having said substituents in the 1-phenyl group attached in the 2, 4 and 6-positions. More preferably, at least two of said substituents in the 2,4- and 6-positions are halogen atoms and more preferably are chlorine atoms. More preferably, they are 3 chlorine atoms.

The acylamino substituents in the 3-position in the 5-pyrazolone nucleus may be substituents of a type known to the man skilled in the art, such as phenylcarbonylamino, phenylureido (or phenylaminocarbonylamino), alkylcarbonylamino, or phenyloxyalkylcarbonylamino, and those described in the patents cited by the Applicant. Preferably, they are substituents corresponding to the formula—$NHCOR_1$, wherein $R_1$ is:

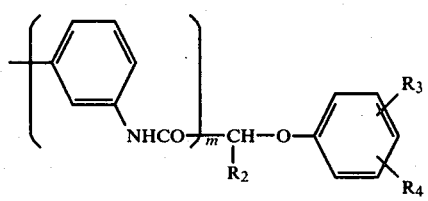

wherein $R_2$ is hydrogen, $CH_3$, $C_2H_5$; $R_3$ and $R_4$ are hydrogen or alkyl having from 1 to 20 carbon atoms, the total of the carbon atoms in $R_3+R_4$ being equal to at least 8 and lower or equal to 20; and m being equal to 0 or 1.

The present invention refers furthermore to a photographic element comprising a supporting base and a plurality of layers, at least one of which is a gelatin silver halide emulsion layer, one of said layers containing at least one of the couplers as per above.

The present invention refers to the above said elements comprising at least a blue-sensitive layer associated with a yellow forming coupler, a green-sensitive layer associated with a magenta (blue+red) forming coupler and a red-sensitive layer associated with a cyan (blue+green) forming coupler, said layers being preferably arranged in the cyan-magenta-yellow order starting from the base with a filter layer coated between the magenta and yellow layers.

Preferably, the photographic element prior to or after the processing thereof respectively contains the couplers or the dyes derived therefrom upon color development dispersed in the layers dissolved in a substantially water-immiscible organic solvent.

The following couplers have been prepared according to two different methods A and B, method A being more suitable for industrial preparations than method B, for reasons which will be clear to the man skilled in the art (see the hereinafter reported description). In particular, method A resulted to be more simple and more suitable to obtain pure products.

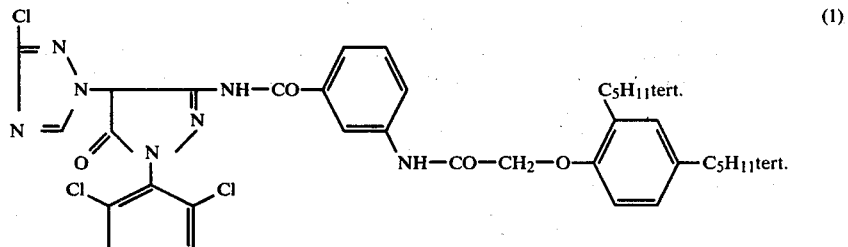

(1)

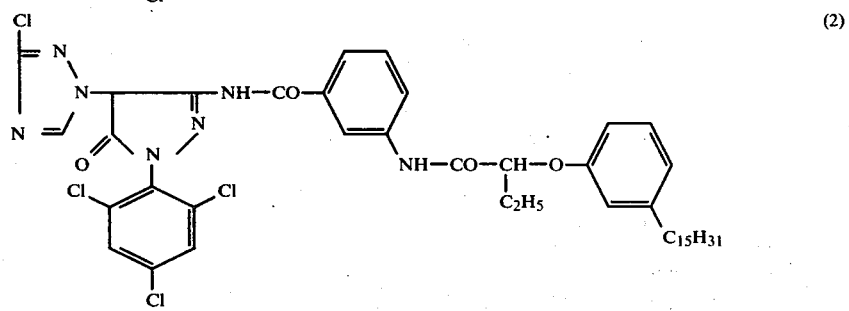

(2)

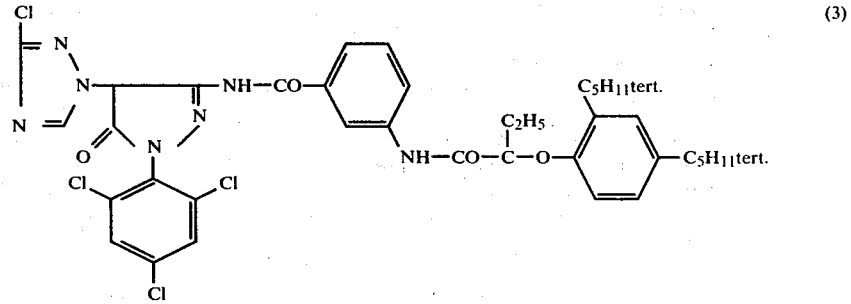

(3)

-continued
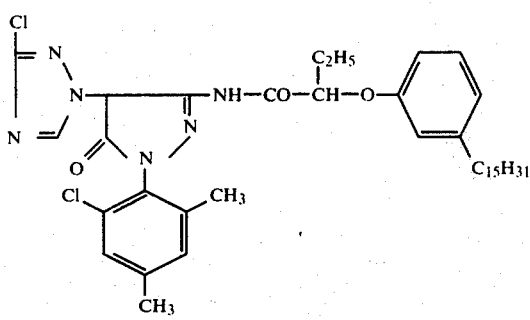
(4)
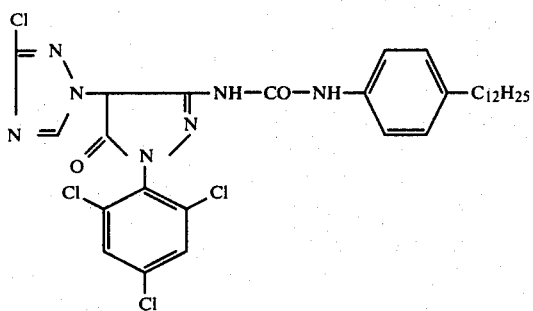
(5)
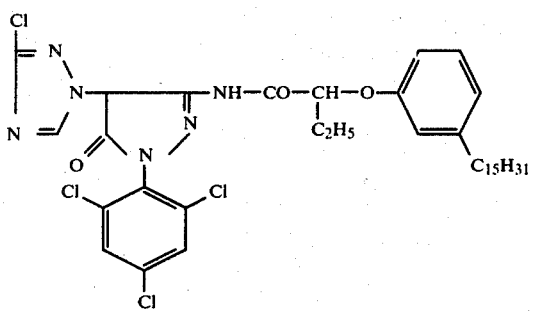
(6)
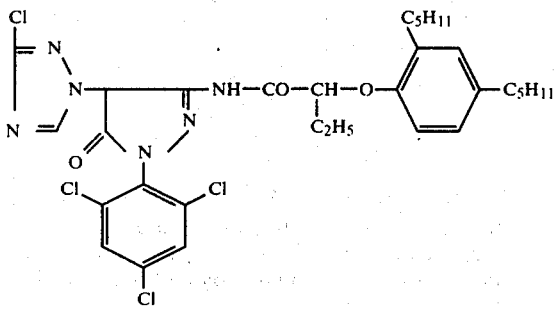
(7)
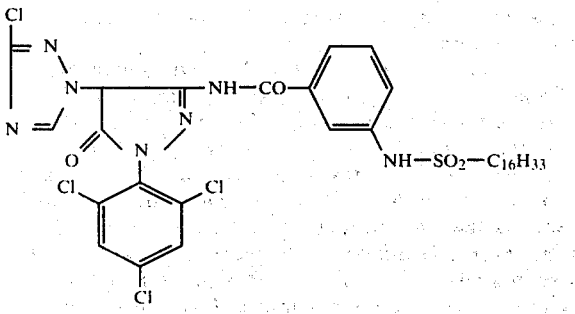
(8)

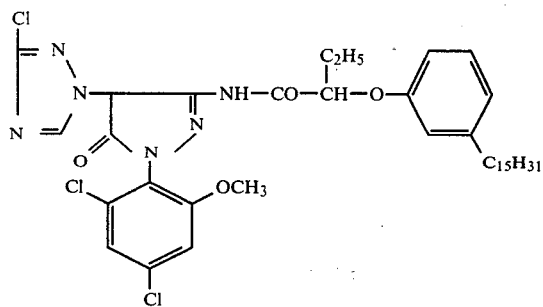 (9)

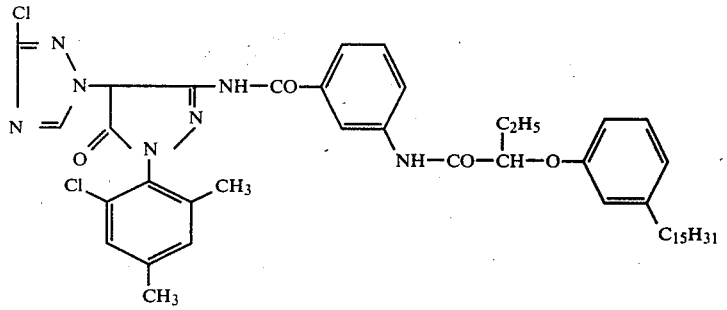 (10)

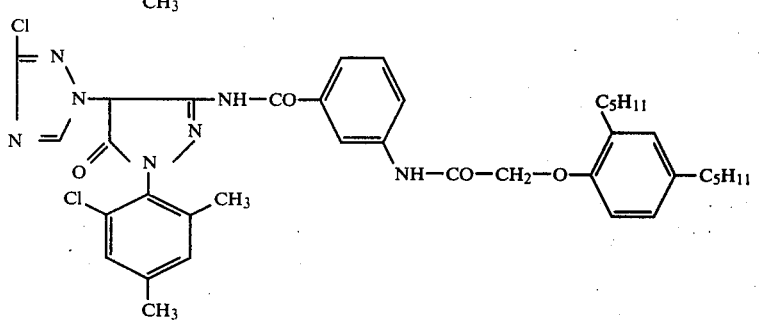 (11)

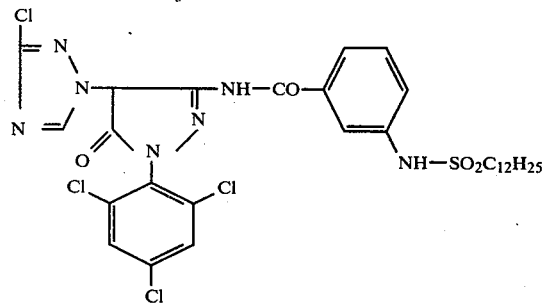 (12)

METHOD A

The couplers of the present invention from 1 to 5 as per above, have been prepared by following such a method starting from the 4-equivalent-5-pyrazolone coupler upon bromination (e.g. with N-bromo-succinimide) and further reaction of the 4-bromo-derivative with a triazole of the type of the present invention, in the presence of an organic solvent, of the dimethylformamide type, and a strong base, of the sodium methylate type, at a temperature ranging from 50° to 120° C. The solid product, obtained by pouring the reaction mass into water and further filtration thereof, has been then purified by crystallizing it from a benzene, toluene, ethyl acetate, acetonitrile type solvent or a mixture thereof, such as e.f. acetonitrile with ethyl acetate.

EXAMPLE 1

Preparation of coupler 1: 1-(2,4,6-trichlorophenyl)-3-/3-α[2,4-ditert.-amylphenoxyacetamido]-butyramido/-4-(3-chloro-1,2,4-triazolyl)-5-pyrazolone (METHOD A).

(a) Preparation of 1-(2,4,6-trichlorophenyl)-3-/3-α[2,4-ditert.-amylphenoxyacetamido]-butyramido/-4-bromo-5-pyrazolone (Intermediate A).

Into a 2,000 ml multi-necked flask, containing 700 ml of acetone, 67.204 g of 1-(2,4,6-trichlorophenyl)-3-/3'-[2,4-ditert.-amylphenoxyacetamido]-butyramido/-5-pyrazolone, equal to 0.1 mole, were introduced under good stirring. To the resulting solution, 175 ml of water and then 19 g of N-bromo-succinimide, equal to 0.1067 mole, in four portions were added thereto. After 10 minutes, 3 g of ascorbic acid were added and the so-obtained mixture was stirred for other 10 minutes. The solution was then poured into a 2,000 ml separatory funnel and 210 ml of water were added thereto. The separated oil was left to settle, then redissolved with very little acetone and finally poured under strong stirring into a beaker containing 1,500 ml of water. The so-obtained yellow solid was then filtered on a Buchner funnel and dried at 50° C. 67 g of the product were obtained. Yield 89.3%.

| Analysis: | Found | Calculated for $C_{34}H_{36}N_4O_4Cl_3Br_2$ |
|---|---|---|
| | C % 54.39 | 54.38 |
| | H % 4.90 | 4.83 |
| | N % 7.47 | 7.46 |
| | Br % 10.27 | 10.64 |

(b) Preparation of 3-chloro-1,2,4-triazole (Intermediate B)

3-chloro-1,2,4-triazole was prepared according to Thiele and Manchot, Liebigs Ann. Chem. Vol. 303, page 50.

(c) Preparation of the coupler

Into a 2,000 ml multi-necked flask, containing 1,400 ml of N,N-dimethylformamide, 209.8 g of intermediate A, equal to 0.2793 mole, and 57.81 g of intermediate B, equal to 0.5586 mole, were introduced under stirring. To the resulting solution, 30.17 g of sodium methylate, equal to 0.5586 mole, were added. The temperature increased of about 20° C. The temperature was rapidly increased up to 100° C. and maintained for 30 minutes. The reaction mass was left to cool at room temperature and then poured into 20,000 ml of cold water. It was then acidified with 37% HCl and the so-formed precipitate was filtered on a Buchner funnel. The so-obtained product was dried at 60° C. and crystallized from 250 ml of toluene. 130 g of a white crystalline product were obtained. Yield: 60.2%.

| Analysis: | Found | Calculated for $C_{36}H_{37}Cl_4N_7O_4$ |
|---|---|---|
| | C % 55.91 | 55.90 |
| | H % 4.80 | 4.82 |
| | N % 12.58 | 12.68 |
| | Cl % 18.36 | 18.33 |

The couplers as per above from 2 to 5 were prepared following Method A, but using the appropriate intermediates. The analytical data of the listed couplers are shown in Table I (a) reaction of an α-halogen-α-carboalkoxy-acetamide with a 1,2,4-triazole, substituted according to the present invention, in the presence of a base;

(b) reaction of the α-triazolyl-α-carboalkoxy-acetamide obtained with phosphorous pentasulfide;

(c) reaction of the α-triazolyl-α-carboalkoxy-thiocetamide obtained with phenylhydrazine and further condensation of the obtained phenylhydrazone in the presence of a base.

EXAMPLE 2

Preparation of coupler 6: 1-(2,4,6-trichlorophenyl)-3-[α-(m-pentadecylphenoxybutyramido]-4-(3-chloro-1,2,4-triazolyl)-5-pyrazolone (METHOD B)

(a) Preparation of α-carbetoxyacetamide (Intermediate C)

200 g of ethyl β-ethoxy-β-iminopropionate hydrochloride were placed into a 1,000 ml flask and heated at 110° C. on an oil bath for 2 hours. The reaction mixture was redissolved with 500 ml of acetone, filtered by washing on the filter with other solvent. The filtrate was dried under vacuum and the obtained oily residue was grinded in 1,500 ml of ethyl ether. 108 g of a crystalline product were obtained. Upon TLC analysis, the product proved to be pure.

(b) Preparation of α-bromo-α-carbetoxyacetamide (Intermediate D)

262 g of intermediate C were dissolved in 2,400 ml of water in a 5,000 ml beaker. The solution was cooled at 7°–8° C. and 288 g of bromine were dropped therein in one hour and a half maintaining the temperature under 10° C. At the end of the addition, the solution was neutralized with 30% NaOH up to a pH=3÷4, using bromophenol blue as an indicator. The product was filtered under vacuum and dried at 60° C. 271 g of the product were obtained. Yield 71.7%.

| Analysis: | Found | Calculated |
|---|---|---|
| | Br % 38.52 | 38.05 |

(c) Preparation of α-(3-chloro-1,2,4-triazolyl)-α-carbetoxyacetamide (Intermediate E)

In a 3,000 ml flask, 103.5 g of 3-chloro-1,2,4-triazole, equal to 1 mole, and 210 g of intermediate D were dissolved in 1,500 ml of anhydrous acetone. The solution was cooled at 3°–4° C. with an external ice bath and 84

TABLE 1

| Coupler No. | Method | Crystall. Solvent | Found C % | H % | N % | Cl % | Calculated C % | H % | N % | Cl % |
|---|---|---|---|---|---|---|---|---|---|---|
| 1 | A | Toluene | 55.91 | 4.80 | 12.58 | 18.36 | 55.90 | 4.82 | 12.68 | 18.33 |
| 2 | A | Toluene | 58.30 | 5.60 | 11.26 | 16.41 | 59.25 | 5.90 | 11.25 | 16.27 |
| 3 | A | Ethylacetate/acetonitrile 1/1 | 56.32 | 5.22 | 12.35 | 17.48 | 56.94 | 5.16 | 12.23 | 17.69 |
| 4 | A | Toluene | 63.18 | 7.30 | 11.33 | 9.64 | 64.12 | 7.36 | 11.81 | 9.69 |
| 5 | A | Ethylacetate/Acetonitrile 2/1 | | | | | | | | |

METHOD B

The couplers of the present invention have been prepared by following an alternative method which consists generally in reacting 3-amino-4-(1,2,4-triazolyl)-5-pyrazolone with an acyl-chloride; such 3-amino-4-(1,2,4-triazolyl)-5-pyrazolone has been obtained by means of the following reactions:

g of powdered NaOH were added thereto all at once. The mixture was kept at <20° for 2 hours and then the solution was acidified with concentrated HCl, the inorganic compounds were filtered on a Buchner funnel washing on the funnel with further acetone, and the filtrate was then evaporated. The so-obtained oily residue was crystallized from water, thus obtaining 127 g of a white product melting at 108°–110° C.

| Analysis: | Found | Calculated |
|---|---|---|
| | C % 36.02 | 36.14 |
| | H % 3.90 | 3.90 |
| | N % 24.04 | 24.09 |
| | Cl % 14.68 | 15.24 | p (d) Preparation of α(3-chloro-1,2,4-triazolyl)-α-carbetoxy-thiocetamide (Intermediate F)

A solution of 46 g of intermediate E, equal to 0.2 mole, in 300 ml of anhydrous dioxane, was added with 11.1 g of $P_2S_5$, equal to 0.05 mole. The mixture was refluxed for one hour and a half, then cooled and filtered. The filtrate was evaporated under vacuum and the residual oil was used for the next reaction without further purification.

(e) Preparation of 1-(2,4,6-trichlorophenyl)-3-amino-4-(3-chloro-1,2,4-triazolyl)-5-pyrazolone (Intermediate G)

Intermediate F was mixed with 53 g of 2,4,6-trichloro-phenyl-hydrazine amd 150 ml of ethyl acetate. The mixture was refluxed for 18 hours and the solvent was evaporated under vacuum. To the resulting residue a solution of 21.1 g of sodium methylate, equal to 0.4 mole, in 400 ml of pure methanol, was added. The solution was refluxed for 15 minutes and poured under stirring into 2,000 ml of cold water. The pH-value of the solution was then adjusted at about 8 with diluted HCl. The solid was filtered, washed with water; the solution was acidified with diluted HCl. The solid, which separated, was filtered, washed with cold water, dried and crystallized from ethanol. 42.5 g of the product were obtained.

| Analysis: | Found | Calculated |
|---|---|---|
| | C % 34.01 | 34.77 |
| | H % 2.08 | 1.59 |
| | N % 21.55 | 22.12 |
| | Cl % 35.16 | 37.32 |

(f) Preparation of the coupler 10 g of intermediate G, 125 ml of acetonitrile and 16.1 g of α-(m-pentadecylphenoxy)-butyrril-chloride were refluxed for 3 hours. The solvent was evaporated under vacuum and the residue was dissolved in 100 ml of ethyl acetate. The solution was vigorously stirred for 10 minutes with a cold solution of 10% NaOH. After neutralization with HCl, the organic layer was separated, washed with water and the solvent was evaporated. The residue was crystallized from a 1:1-ethylacetate/acetonitrile mixture, thus obtaining 18.2 g of a white product.

| Analysis: | Found | Calculated |
|---|---|---|
| | C % 56.83 | 57.45 |
| | H % 6.02 | 6.16 |
| | N % 10.61 | 11.7 |

| Analysis: | Found | Calculated |
|---|---|---|
| | Cl % 18.25 | 18.84 |

Couplers 4, 7 and 9 were prepared in a similar way but using different appropriate intermediates. The analytical data of such couplers are shown in Table 2.

TABLE 2

| Coupler No. | Method | Crystall. solvent | Found | | | | Calculated | | | |
|---|---|---|---|---|---|---|---|---|---|---|
| | | | C % | H % | N % | Cl % | C % | H % | N % | Cl % |
| 6 | B | Ethylacetate Acetonitrile 1/1 | 56.83 | 6.02 | 10.61 | 18.25 | 57.45 | 6.16 | 11.17 | 18.84 |
| 7 9 (°) | B | Acetonitrile | 51.79 | 5.18 | 10.77 | 17.82 | 54.56 | 5.32 | 12.31 | 20.78 |

(°) Upon a silica gel TLC analysis, such coupler proved to be pure.

EXAMPLE 3

Preparation of coupler 1 : 1-(2,4,6-trichlorophenyl)-3-[3-α-(2,4-ditert.-amylphenoxy-acetamido)-butyramido]-4-(3-chloro-1,2,4-triazolyl)-5-pyrazlone (METHOD B)

(a) Preparation of 1-(2,4,6-trichlorophenyl)-3-(3-nitro-benzamido)-4-(3-chloro-1,2,4-triazolyl)-5-pyrazolone (Intermediate H)

37.1 g of intermediate G of Example 2, equal to 0.098 mole, 500 ml of acetonitrile and 27.2 g of m-nitrobenzoyl chloride, equal to 0.147 mole, were put into a 1,000 ml flask. The mixture was refluxed for one hour and a half, the solvent was then evaporated under vacuum and the residue was stirred with 300 ml of a cold 3% NaOH solution. The obtained turbid solution was filtered and acidified with concentrated HCl. The solid was filtered, washed with water, dried and purified by digestion with boiling acetonitrile, thus obtaining a yellow solid melting at 245° C., with decomposition.

| Analysis: | Found | Calculated |
|---|---|---|
| | O % 40.73 | 40.86 |
| | H % 1.65 | 1.71 |
| | N % 17.78 | 18.53 |
| | Cl % 25.99 | 26.80 |

(b) Preparation of 1-(2,4,6-trichlorophenyl)-3-(3-aminobenzamido)-(3-chloro-1,2,4-triazolyl)-5-pyrazolone (Intermediate I)

26.4 g of Intermediate H were dissolved in 250 ml of methyl-cellosolve and reduced at 50° C. with $H_2$ at 20 atmospheres and Ni Raney. After cooling, Ni was filtered and the solvent was evaporated under vacuum. The resulting solid was extracted with boiling ethanol and filtered, thus obtaining 18 g of a white solid melting t 252° C.

(c) Preparation of the coupler 5 g of intermediate 1 equal to 0.01 mole, were dissolved in 50 ml of acetonitrile and mixed with 3 g of α-(2,4-ditert. -amylphenoxy) -butyrril-chloride. The mixture was refluxed for two hours and then poured into cold water. The white precipitate, thus obtained, was filtered, washed with cold water, dried and purified by crystallization for ethyl acetate/acetonitrile. A white crystalline solid was obtained. M.P. : 215° C.

| Analysis: | Found | Calculated |
|---|---|---|
| | C % 55.42 | 55.90 |
| | H % 4.86 | 4.82 |
| | N % 12.5 | 12.67 |
| | Cl % 18.14 | 18.33 |

Couplers 2, 3, 8, 10, 11 and 12 were prepared in a similar way as that described for coupler 1 of example 3, but using the appropriate intermediates. The analytical data of such couplers are shown in Table 3.

TABLE 3

| Coupler No. | Method | Crystall. solvent | Found C % | H % | N % | Cl % | Calculated C % | H % | N % | Cl % |
|---|---|---|---|---|---|---|---|---|---|---|
| 2(*) | B | | | | | | | | | |
| 3(*) | B | | | | | | | | | |
| 4 | B | Toluene | | | | | | | | |
| 5(*) | B | Ethylacetate Acetonitrile 2/1 | | | | | | | | |
| 8(*) | B | | | | | | | | | |
| 10 | B | — | 63.63 | 6.89 | 11.24 | 9.38 | 65.05 | 6.91 | 11.80 | 8.54 |
| 11 | B | — | 59.52 | 5.63 | 12.82 | 11.62 | 62.29 | 5.92 | 13.38 | 9.68 |
| 12(*) | B | | | | | 19.84 | | | | 19.39 |

(*) Upon silica gel TLC analysis, products produ proved to be pure.

The couplers of the present invention may be used in association with many types of silver halide emulsions suitable for color photography. They can be used for instance with silver bromide, silver chloride or silver iodide emulsions or with those emulsions containing a halide mixture, such as silver bromo-iodide or silver chloro-bromide emulsions. The couplers can also be used with those emulsions which are described in U.S. Pat. No. 2,592,243 or 2,698,794. Such couplers can still be used with those emulsions capable of forming an image on the surface or in the interior of the silver halide grains, such as those described in U.S. Pat. No. 2,592,250.

When the couplers of the present invention are included in photographic elements (prior to their exposure and development), they can be directly introduced into the emulsions before their coating on photographic base into a layer adjacent thereto.

As it is known to the man skilled in the art, the above mentioned emulsions can be chemically sensitized either by addition of sulfur compounds, as described for instance in U.S. Pat. No. 1,574,944, 1,623,469, 2,410,689; and by addition of noble metal salts, such as rhutenium, rhodium, iridiium, palladium and platinum. Such emulsions can be chemically sensitized by addition of Au salts, as described in U.S. Pat. No. 2,399,083. They can be stabilized with Au salts as described in U.S. Pat. No. 2,597,856 and 2,587,915.

The above emulsions can be optically sensitized with carbocyanine dyes such as those described for example in U.S. Pat. No. 2,503,776.

The emulsions can contain organic stabilizers and antifoggants of the cyclic amine type; iminoazoles such as mercapto-benzimidazole; triazoles such as those described in U.S. Pat. No. 2,444,608; azaindenes such as those described in U.S. Pat. No. 2,444,605, 2,444,606, 2,444,609, 2,450,397, 2,713,541, 2,716,062, 2,735,769, 2,743,181, 2,756,147, 2,772,164 and E. J. Birr, Z. Wiss. Phot. 472 (1952); tetrazoles such as 1-phenyl-5mercapto-tetrazole; thiazoles and benzothiazoles such as 1-methyl-benzothiazole and benzothiazole quaternary salts, as described in U.S. Pat. No. 2,131,038; mercapto-benzothiazoles such as 1-methyl-mercapto-benzo-thiazole; oxazoles, thiosemicarbazydes; pyrimidines; iodonium derivatives; benzensulphynic acids; inorganic stabilizers of the zinc and cadmium salt type such as those described in U.S. Pat. No. 2,839,405.

The emulsions can further contain any suitable plasticizer known to the man skilled in the art such as glycerin.

The emulsion may be hardened with any suitable hardener for gelatin, known to the man skilled in the art such as aldehyde of the formaldehyde, glyoxale, succinic, glutaric and resorcylic aldehyde type; and halogen substituted aliphatic acids such as mucochloric and mucobromic acids as described in U.S. Pat. No. 2,080,019; or mixture thereof as described in U.S. Pat. No. 2,591,542.

The emulsions may have been supplied with a coating aid, known to the man skilled in the art such as saponin. Any suitable base type, known to the man skilled in the art, can be used, such as cellulose triacetate, polyester, paper, polytenated paper. In the preparation of the silver halide dispersions, employed for preparing silver halide emulsions, there may be employed as the dispersing agent for the silver halide in its preparation, gelatin or another water-permeable means of the colloidal albumin type, a cellulose derivative, or a synthetic resin of the polyvinyl type. Such material types are described in U.S. Pat. No. 2,286,215, 2,328,808, 2,322,085, 2,527,872, 2,541,474, 2,563,791, 2,768,154, 2,808,331, 2,852,382. If desired a mixture of two or more of these colloids may be employed for dispersing the silver halide in its preparation.

The couplers of the present invention, used alone or in combination with 4-equivalent couplers, proved to be particularly useful in a color photographic material of the negative type using the masking technique (includeing masked couplers further to main couplers as for instance described in U.S. Pat. No. 2,428,054, 2,808,329, 2,860,975 and 2,852,370) and the double layer technique (as for example described in G.B. Pat. No. 818,687).

In addition to the main couplers and masked couplers, other additional couplers can be used, such as for instance the couplers described in U.S. Pat. No. 2,689,793, 2,742,832, 2,998,314 and 3,227,554.

The developing baths to be used in conjunction with the couplers of the invention are well-known to the man skilled in the art. They contain a developer of the p-phenylene diamine type, a development restrainer of the potassium bromide type, an antioxidant, such as sodium sulfite and an alkaline agent of the alkali hydrate or carbonate type. They may further contain both an antifoggant of the benzimidazole type and derivatives, of the benzothiazole type and derivatives, of the triazole and tetrazole type and derivatives, such as mercaptoderivatives; and an anti-calcium substance of the alkaline phosphate and alkylendiamino-acetic acid type, such as for instance EDTA. Compounds known to the man skilled in the art, of the p-phenylene-diamine type, are those described for instance in U.S. Pat. Nos. 2,193,015, 2,656,273, 2,875,049 and C. E. Kenneth Mees and T. H. James, The Theory of the Photographic Process, third edition, table 13.4, pages 294–295.

Suitable developers, which can be employed to develop photographic elements, containing the couplers of the present invention, are the sulfites, the hydro-chlorides and the sulfates of:

(a) N,N-diethyl-p-phenylene diamine
(b) N-ethyl,N-β-methansulfonamido-ethyl-3-methyl-4-amino aniline
(c) N-ethyl,N-hydroxyethyl-2-methyl-p-phenylene diamine
(d) N-ethyl,N-hydroxyethyl-p-phenylene diamine
(e) N,N-diethyl-2-methyl-p-phenylene diamine.

The following couplers, outside of the scope of the present invention, have been tested with the couplers of the present invention for comparison purposes:

couplers D, E, F and G hereinafter described (Method A). Couplers H, I, L and M have been prepared as described in U.S. Application Ser. No. 885,208 of the Applicant.

EXAMPLE 4

Samples of an orthochromatically sensitized silver bromo-iodide negative photographic emulsion were added (according to the dispersion technique by using n-dibutylphtalate as solvent) with the 2-equivalent magenta couplers No. 3 and B in a quantity of 83.13 mM/Ag mole. The finally obtained emulsions were then coated on a cellulose triacetate base at a silver covering weight of 1.1 g/m². Similarly a further sample of the same emulsion was added with the 4-equivalent magenta coupler A in a quantity of 41.56 mM/Ag mole and then coated on a supporting base, as above, at a silver covering weight of 2.2 g/m². The obtained sensitometric samples were exposed at a sensitometer normalized with a 0.30 logit gradient wedge, at a color temperature of 5,500° K. They were then developed, at the same time, in a standard developer for color nega-

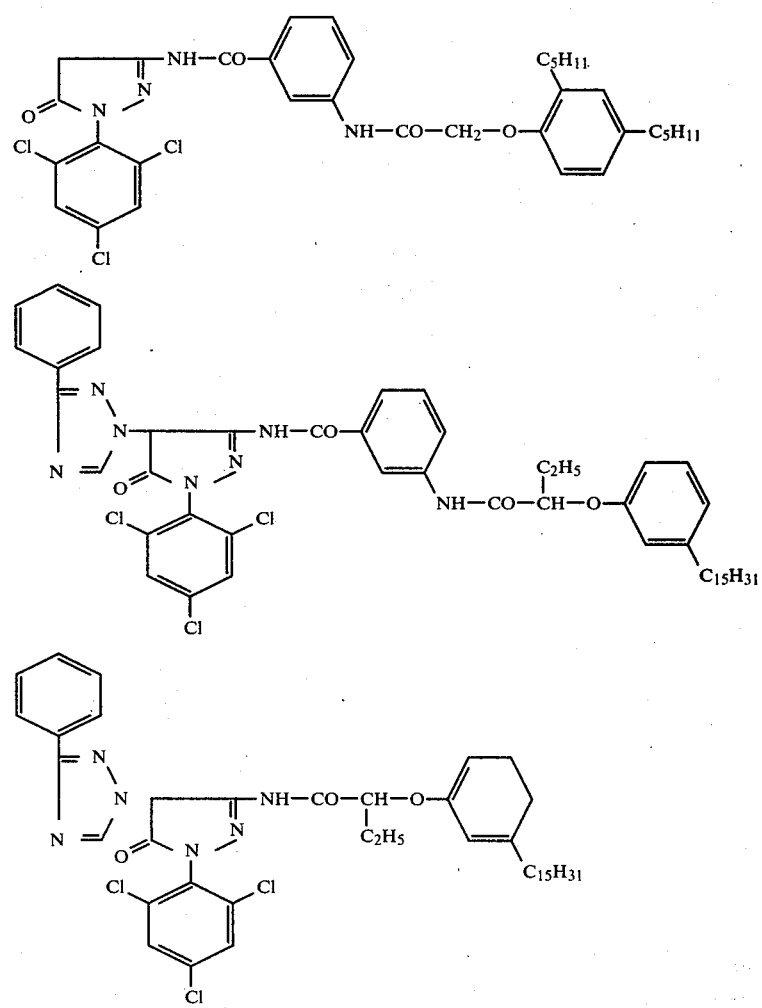

Coupler A is very known in the art (as per U.S. Pat. No. 2,600,788) and can be prepared with a well-known method. Couplers B and C have been prepared (Method B) in a similar way as the couplers of the present invention, with which they have been compared, as well as tive films (C 41 type) and finally read with an automatic densitometer, thus obtaining the following results (pls. see Table 4 and additionally note that coating including coupler 2 showed finer grain and better modulated contrast with respect to A and B):

TABLE 4

| Coupler | Fog | Sensitivity 10·(log E) | $D_{max}$ |
|---|---|---|---|
| 2 | 0.32 | 14.1 | 2.05 |
| A | 0.14 | 16.8 | 1.58 |
| B | 0.72 | 18.3 | 2.48 |

EXAMPLE 5

Material samples containing 2-equivalent magenta couplers in comparison with a 4-equivalent coupler of reference (coupler A) were made in a similar way as those of example 4. The so-obtained samples, after incubation on shelf (i.e. at room conditions) or under particular conditions (38° C. and high relative humidity), were exposed and processed in a similar way as done in example 4. The following results were obtained.

TABLE 5

| Coupler | Fog Shelf; | Fog Incubated (*) | Sensitivity 10·(log E) Shelf; | Sensitivity 10·(log E) Incubated (*) | $D_{max}$ $D_1$ Shelf; | $D_{max}$ $D_2$ Incubated (*) | Δ % $(D_1-D_2)\cdot 100$ |
|---|---|---|---|---|---|---|---|
| A | 0.14 | 0.11 | 17.3 | 17.4 | 1.03 | 0.82 | 20.4 |
| C | 0.54 | 0.44 | 14.6 | 15.6 | 2.29 | 2.36 | −3.0 |
| 1 | 0.17 | 0.15 | 15.7 | 15.5 | 2.05 | 1.91 | 6.8 |
| 2 | 0.29 | 0.27 | 15.3 | 15.7 | 2.21 | 2.19 | 0.9 |
| 3 | 0.24 | 0.24 | 17.1 | 17.6 | 2.42 | 2.43 | −0.4 |
| 5 | 0.29 | 0.25 | 16.6 | 16.6 | 1.91 | 1.87 | 2.1 |
| 6 | 0.30 | 0.29 | 16.8 | 17.6 | 2.61 | 2.58 | 1.1 |

(*) 7 days at 38° C.

EXAMPLE 6

Coatings have been prepared as follows:

(a) 2 g of each coupler were dissolved in 4 ml of n-dibutylphtalate and 12 ml of ethylacetate, emulsified with an aqueous solution of gelatin, mixed with a chlorobromide photographic emulsion, coated on a transparent base and dried. Each coating of the couplers 1, 3, I, L and H contained approximately 9.2 $10^{-3}$ moles of silver and 3.1 $10^{-3}$ moles of coupler per square meter, while the coating of the coupler A contained approximately $18.4 \cdot 10^{-3}$ moles of silver and $3.1 \cdot 10^{-3}$ moles of coupler per square meter.

(b) 2 g of each coupler were dissolved in 4 ml of dibutyl-formamide and 12 ml of ethylacetate, emulsified and coated as described in a). Each coating of the couplers G, E and M contained approximately $9.2 \cdot 10^{-3}$ moles of silver and $3.1 \cdot 10^{-3}$ moles of coupler per square meter.

(c) 2 g of each coupler were dissolved in a mixture of 2 ml of tricresyl-phosphate, 2ml of diethyllauramide, 1.6 ml of dibutylformamide and 12 ml of ethylacetate, emulsified and coated as described above in (a). Each coating of the couplers D and F contained approximately $9.2 \cdot 1.0^{-3}$ moles of silver and $3.1 \cdot 10^{-3}$ moles of coupler per square meter.

A sample of each coated emulsion as per above was identically exposed to light and processed in C 41 type process for color negative (Developer 1) as normally found in the market. Tables 6 and 7 show the sensitometric data of the so obtained magenta images.

A further sample of each coated emulsion was identically exposed to light and developed for 8 minutes at 24° C. in the Developer 2 having the following composition:

| | |
|---|---|
| 2-amino-5-diethylamino-toluene-hydrochloride | 3.0 g |
| anhydrous sodium sulfite | 4.0 g |
| anhydrous sodium carbonate | 18.0 g |
| potassium bromide | 2.0 g |
| sodium examethaphosphate | 2.0 g |
| water to make | 1.0 l |

After the silver image and the residual silver halide were removed by treatment with a conventional ferricyanine bleach followed by a hypo-fixing bath, a negative magenta image was obtained, whose sensitometric data are shown in Tables 6 and 7.

TABLE 6

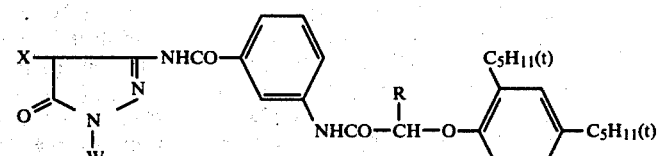

| | | | | DEVELOPER 1 | | | | DEVELOPER 2 | | | |
|---|---|---|---|---|---|---|---|---|---|---|---|
| Coup. | R | X | Disp. | Fog | $D_{max}$ | α | Speed (−Δ log E) | Fog | $D_{max}$ | α | Speed (−Δ log E) |
| 1 | H | 3-Cl-1,2,4-triazole | a | 0.19 | 2.98 | 3.00 | −0.15 | 0.15 | 3.47 | 2.43 | +0.17 |
| 3 | $C_2H_5$ | 3-Cl-1,2,4-triazole | a | 0.18 | 2.92 | 2.92 | −0.03 | 0.13 | 3.52 | 3.35 | −0.07 |
| G | $C_2H_5$ | 3-Me-1,2,4-triazole | b | 0.11 | 1.14 | 0.80 | −0.73 | 0.25 | 1.66 | 1.0 | −0.72 |
| D | H | 3-Cl-5-Me-1,2,4-triazole | c | 0.05 | 0.09 | — | — | 0.05 | 0.15 | — | — |
| E | H | imidazole | b | 0.07 | 0.19 | — | — | 0.05 | 0.19 | — | — |
| F | $C_2H_5$ | 3,5-diMe-1,2,4-triazole | c | 0.05 | 0.07 | — | — | 0.11 | 0.29 | — | — |

TABLE 6-continued

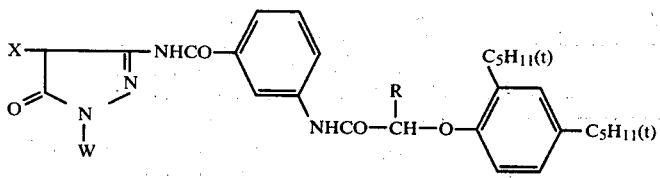

| | | | | | DEVELOPER 1 | | | DEVELOPER 2 | | |
|---|---|---|---|---|---|---|---|---|---|---|
| Coup. | R | X | Disp. | Fog | $D_{max}$ | α | Speed ($-\Delta \log E$) | Fog | $D_{max}$ | α | Speed ($-\Delta \log E$) |
| A | H | H | a | 0.27 | 2.96 | 2.53 | 0.0 | 0.10 | 2.86 | 2.1 | 0 |

W = 2,4,6-trichlorophenyl

TABLE 7

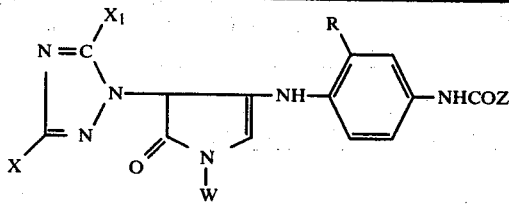

| | | | | | | DEVELOPER 1 | | | DEVELOPER 2 | | |
|---|---|---|---|---|---|---|---|---|---|---|---|
| Coup. | X | $X_1$ | R | Z | Disp. | Fog | $D_{max}$ | α | Speed ($-\log E$) | Fog | $D_{max}$ | Speed ($-\log E$) |
| I (*) | Cl | Me | H | $Z_1$ | a | 0.13 | 2.80 | 1.70 | −0.10 | 0.10 | 3.08 | 2.80 | −0.03 |
| L (*) | Cl | Me | H | $Z_2$ | a | 0.14 | 2.48 | 1.60 | −0.15 | 0.11 | 3.10 | 2.20 | 0 |
| M (*) | Cl | Me | Cl | $Z_2$ | b | 0.15 | 2.92 | 1.70 | +0.05 | 0.19 | 3.91 | 3.70 | +0.10 |
| H (*) | Cl | H | Cl | $Z_1$ | a | 2.40 | 3.95 | — | — | 0.50 | 3.78 | >5.00 | — |

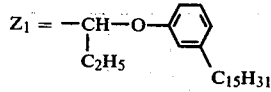

W = 2,4,6-trichlorophenyl

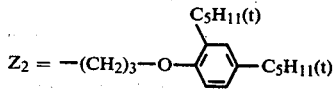

(*) These couplers have been prepared as described in the cited U.S. Application S. N. 885,208.

I claim:

1. A photographic element including a supporting base and a plurality of layers, at least one of said layers being a gelatin silver halide emulsion layer; said element characterized by at least one of said layers contains a two equivalent 1-phenyl-3-acylamino-5-pyrazolone photographic coupler compound characterized by having, attached in the 4-position, a 1,2,4-triazole group substituted in the 3-position with a halogen atom and having a hydrogen atom in the 5-position, said phenyl group in the 1-position, said phenyl group in the 1-position of the 5-pyrazolone having at least one halogen atom as a substituent.

2. The photographic element of claim 1 wherein said coupler compound is dissolved in a substantially water immiscible organic solvent which is dispersed in said at least one gelatin silver halide emulsion layer.

3. The photographic element of claim 1 wherein said coupler compound is present in said at least one gelatin silver halide emulsion layer.

4. The photographic element of claims 1 or 2 including a supporting base, a blue-sensitive emulsion layer associated with a yellow-forming coupler, a green-sensitive layer associated with a magenta-forming coupler which comprises said 1-phenyl-3-acylamino-5-pyrazolone coupler, and a red-sensitive layer associated with a cyan-forming coupler.

5. The photographic element of claims 2 or 3 wherein said 1-phenyl group is substituted with (1) chlorine or bromine in the 2-position and (2) substituents selected from the class consisting of hydrogen, chlorine, bromine, alkyl and alkoxy groups of 1 to 3 carbon atoms in the 4- and 6-positions.

6. The photographic element of claims 2 or 3 wherein said 1-phenyl group has substituents in the 2- and 4-positions selected from chlorine and bromine.

7. The photographic element of claims 2 or 3 wherein said 1-phenyl group is substituted with chlorine in the 2- and 4-positions.

8. The photographic element of claims 2 or 3 wherein said 2-phenyl group is substituted with chlorine in the 2-, 4-, and 6-positions.

9. The photographic element of claims 1, 2 or 3 wherein said 3-acylamino group corresponds to the formula —NH—CO—$R^1$, wherein $R^1$ is

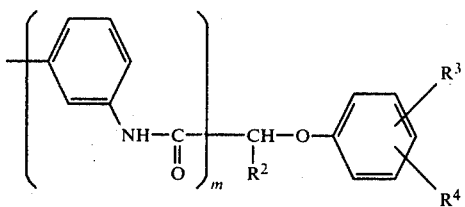

wherein
- $R^2$ is selected from the group of hydrogen, $CH_3$ and $C_2H_5$,
- $R^3$ and $R^4$ are selected from the group of hydrogen and alkyl having from 1 to 20 carbon atoms, the total of the carbon atoms in $R^3 + R^4$ being equal to at least 8 and lower or equal to 20, and m is equal to 0 or 1.

10. The photographic element of claim 4 wherein said 3-acylamino group corresponds to the formula —NH—CO—$R^1$, wherein $R^1$ is

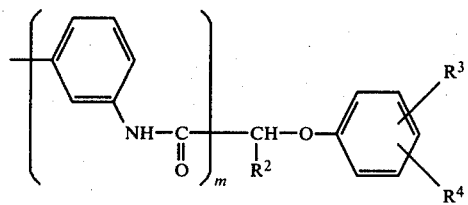

wherein $R^2$ is selected from the group of hydrogen, $CH_3$ and $C_2H_5$,
$R^3$ and $R^4$ are selected from the group of hydrogen and alkyl having from 1 to 20 carbon atoms, the total of the carbon atoms in $R^3 + R^4$ both equal to at least 8 and lower or equal to 20, and
m is equal to 0 or 1.

11. The photographic element of claim 5 wherein said 3-acylamino group corresponds to the formula —NH—CO—$R^1$, wherein $R^1$ is

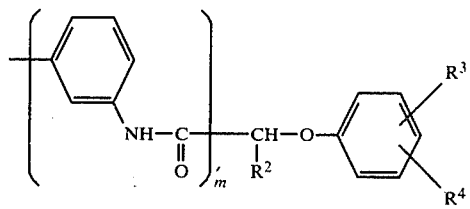

wherein $R^2$ is selected from the group of hydrogen, $CH_3$ and $C_2H_5$,
$R^3$ and $R^4$ are selected from the group of hydrogen and alkyl having from 1 to 20 carbon atoms, the total of the carbon atoms in $R^3 + R^4$ being equal to at least 8 and lower or equal to 20, and
m is equal to 0 or 1.

12. The photographic element of claim 8 wherein said 3-acylamino group corresponds to the formula —NH—CO—$R^1$, wherein $R^1$ is

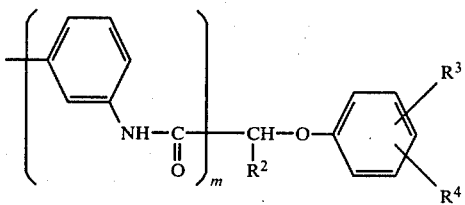

wherein $R^2$ is selected from the group of hydrogen, $CH_3$ and $C_2H_5$,
$R^3$ and $R^4$ are selected from the group of hydrogen and alkyl having from 1 to 20 carbon atoms, the total of the carbon atoms in $R^3 + R^4$ being equal to at least 8 and lower or equal to 20, and
m is equal to 0 or 1.

* * * * *

UNITED STATES PATENT AND TRADEMARK OFFICE
CERTIFICATE OF CORRECTION

PATENT NO. : 4,262,087
DATED : April 14, 1981
INVENTOR(S) : Andrea Quaglia

It is certified that error appears in the above—identified patent and that said Letters Patent is hereby corrected as shown below:

Col. 12, line 59, delete "t" and insert --at--.

Col. 20, line 64, delete "2-phenyl" and insert --1-phenyl--.

Signed and Sealed this

Twelfth Day of January 1982

[SEAL]

Attest:

GERALD J. MOSSINGHOFF

Attesting Officer    Commissioner of Patents and Trademarks